(12) United States Patent
Goebbel et al.

(10) Patent No.: US 7,692,031 B2
(45) Date of Patent: Apr. 6, 2010

(54) SEPARATION OF PROPYLENE OXIDE FROM A MIXTURE COMPRISING PROPYLENE OXIDE AND METHANOL

(75) Inventors: Hans-Georg Goebbel, Kallstadt (DE); Henning Schultz, Mannheim (DE); Peter Schultz, Bad Duerkheim (DE); Renate Patrascu, Stade (DE); Malte Schulz, Hollern-Tw. (DE); Meinolf Weidenbach, Drochtersen (DE)

(73) Assignees: BASF Aktiengesellschaft, Ludwigshafen (DE); The Dow Chemical Company, Midland, MI (US)

( * ) Notice: Subject to any disclaimer, the term of this patent is extended or adjusted under 35 U.S.C. 154(b) by 521 days.

(21) Appl. No.: 11/631,843

(22) PCT Filed: Jul. 6, 2005

(86) PCT No.: PCT/EP2005/007299
§ 371 (c)(1),
(2), (4) Date: Jan. 8, 2007

(87) PCT Pub. No.: WO2006/003003
PCT Pub. Date: Jan. 12, 2006

(65) Prior Publication Data
US 2009/0118523 A1    May 7, 2009

Related U.S. Application Data

(63) Continuation-in-part of application No. 10/884,967, filed on Jul. 7, 2004, now abandoned.

(51) Int. Cl.
*C07D 301/32* (2006.01)
(52) U.S. Cl. .......... 549/541; 549/531; 203/92; 203/96
(58) Field of Classification Search ........... 549/541, 549/531, 542; 203/92, 96, 29, 38, 14, 18, 203/78, 80
See application file for complete search history.

(56) References Cited

U.S. PATENT DOCUMENTS

| | | | |
|---|---|---|---|
| 4,140,588 | A | 2/1979 | Schmidt |
| 5,374,300 | A | 12/1994 | Kaschemekat et al. |
| 5,620,568 | A | 4/1997 | Smith et al. |
| 5,849,938 | A | 12/1998 | Rueter et al. |
| 6,500,311 | B1 | 12/2002 | Sawyer |
| 6,838,587 | B2 | 1/2005 | Lattner et al. |
| 7,323,579 | B2 | 1/2008 | Göbbel et al. |
| 2004/0006239 | A1* | 1/2004 | Haas et al. ......... 549/531 |
| 2006/0113180 | A1 | 6/2006 | Patrascu et al. |

FOREIGN PATENT DOCUMENTS

| | | |
|---|---|---|
| DE | 118 873 | 3/1976 |
| DE | 198 35 907 | 2/2000 |
| EP | 0 311 983 | 4/1989 |
| EP | 0 405 978 | 1/1991 |
| EP | 0 811 617 A1 | 12/1997 |
| EP | 1 424 332 A1 | 6/2004 |
| WO | 98 55228 | 12/1998 |
| WO | 02 14298 | 2/2002 |
| WO | WO 2004/092150 A1 | 10/2004 |

* cited by examiner

*Primary Examiner*—Bernard Dentz
*Assistant Examiner*—David E Gallis
(74) *Attorney, Agent, or Firm*—Oblon, Spivak, McClelland, Maier & Neustadt, L.L.P.

(57) ABSTRACT

A method of separating propylene oxide from a mixture (M) comprising propylene oxide and methanol, said method comprising: (i) introducing said mixture (M) into an extractive distillation column; (ii) additionally introducing an extracting solvent into said extractive distillation column; (iii) distilling propylene oxide overhead from said extractive distillation column as top stream; (iv) withdrawing a bottoms stream from said extractive distillation column; (v) compressing the top stream obtained overhead in (iii) by means of at least one compressor to give a compressed vapor.

19 Claims, 5 Drawing Sheets

SEPARATION OF PROPYLENE OXIDE FROM A MIXTURE COMPRISING PROPYLENE OXIDE AND METHANOL

FIELD OF THE INVENTION

The present invention provides a method of separating propylene oxide from a mixture (M) comprising propylene oxide and methanol, said method comprising
(i) introducing said mixture (M) into an extractive distillation column;
(ii) additionally introducing an extracting solvent into said extractive distillation column;
(iii) distilling propylene oxide overhead from said extractive distillation column as top stream;
(iv) withdrawing a bottoms stream from said extractive distillation column;
(v) compressing the top stream obtained overhead in (iii) by means of at least one compressor to give a compressed vapor.

According to a preferred embodiment of the present invention, the mixture (M) is formed by a reaction of propene with hydrogen peroxide in methanol as solvent and in the presence of a titanium zeolite fixed-bed catalyst. Therefore, the present invention also provides a method of preparing propylene oxide, wherein said reaction comprises reacting propene with hydrogen peroxide in methanol as solvent and in the presence of a titanium zeolite fixed-bed catalyst. This epoxidation reaction results, either directly or after at least one work-up step, in a mixture (M) which preferably comprises from 5 to 50 percent by weight propylene oxide and from 50 to 85 percent by weight methanol, and the method of the present invention further comprises
(i) introducing said mixture (M) into an extractive distillation column;
(ii) additionally introducing an extracting solvent into said extractive distillation column;
(iii) distilling propylene oxide overhead from said extractive distillation column as top stream;
(iv) withdrawing a bottoms stream from said extractive distillation column;
(v) compressing the top stream obtained overhead in (iii) by means of at least one compressor to give a compressed vapor.

BACKGROUND OF THE INVENTION

In numerous publications on the subject of the preparation of propylene oxide, there are only a few which are concerned with integrated processes in which the energy of the vapor obtained in a distillation step is usefully returned to the process. This applies particularly to processes in which propylene oxide is separated off from solvents or traces of solvent by distillation.

WO-A-02/14298 describes a process for the continuous preparation of an olefin oxide. In the context of this process step, it is disclosed that the heat of condensation obtained at the top of a column can be recovered for one or all distillation processes of the overall process. In the column in question, a mixture comprising solvent, oxygen and inert gas is separated by distillation. Specific procedures for recirculating the heat of condensation are not disclosed.

WO-A-00/07965 describes a process for preparing propylene oxide, in which a mixture of propene, propylene oxide and methanol is separated off from a mixture via the top of a distillation column, with the reflux necessary for the separation in the column being condensed in a partial condenser at the top of the column.

If methanol, for example, is used as solvent in the preparation of propylene oxide from propene, it is generally advantageous for this to be used in the reaction section, i.e. for the reaction of propene with a hydroperoxide such as hydrogen peroxide, particularly when a titanium silicalite catalyst of the TS-1 type is used as catalyst for the reaction. On the other hand, the presence of methanol makes purification of the propylene oxide more difficult.

According to the prior art, at atmospheric pressure or superatmospheric pressures, essentially in the range from 1 to 5 bar, propylene oxide and methanol can be separated by distillation only when a distillation column having a very large number of theoretical plates is used and a very high reflux ratio is set at the same time, owing to the entraining azeotrope.

The separation task is simpler at lower pressures, but the low pressure has an adverse effect on the condensation temperature since the condensation temperature, which can, for example, be in the region of 15° C. depending on the pressure, requires provision of a high refrigeration power for condensation. Especially on an industrial scale, this incurs tremendous costs.

Other documents of the prior art relate to process where propylene oxide is separated from the solvent methanol by extractive distillation processes.

U.S. Pat. No. 5,849,938 discloses a process where propylene oxide is separated from methanol in a crude olefin epoxidation product by means of an extractive distillation wherein a relatively heavy polar solvent having hydroxy groups such as water or propylene glycol is used as the extracting solvent, propylene glycol being particularly preferred. According to this document of the prior art, the distillation column used ordinarily has from 20 to 60 theoretical plates, and the reflux/distillate ratio is generally in the range of from 5 to 15. According to the examples, a typical ratio is 9. Typical bottoms temperatures are in the range of 90 to 120° C., the pressure under which distillation is carried out being from 0.55 to 3.44 bar. According to the example, a preferred bottom pressure of the distillation column is 2.76 bar and therefore well above standard pressure. As typical propylene oxide fractions, fractions are obtained comprising 300 or 1,500 ppm of methanol. The bottoms streams obtained according to the examples comprise up to 6,300 ppm of propylene oxide. The purified propylene oxide stream obtained from the process according too U.S. Pat. No. 5,849,938 may be further purified and thus be subjected to a fractional distillation subsequently after removing the propylene oxide stream from the extractive distillation column.

U.S. Pat. No. 6,500,311 B1 discloses a process wherein a separation of methanol and propylene oxide takes place. As extracting solvent, a non-polar solvent, namely a C7-C9 hydrocarbon such as n-octane is used.

It is an object of the present invention to provide a method of separating propylene oxide from methanol which, compared to the processes described in the prior art, has an improved energy balance and, additionally, leads to top streams and bottoms streams having a lesser degree of impurity with regard to methanol and propylene oxide, respectively.

It is a further object of the present invention to provide a method of separating propylene oxide from methanol in which a cheap extracting solvent is employed which simultaneously allows for milder distillation conditions than those described in the prior art.

It is still another object of the present invention to provide a method which, compared to the processes described in the prior art, for example processes for separating propylene oxide from methanol or for preparing propylene oxide, has a significantly improved energy balance.

It is yet another object of the present invention to provide a method of producing propylene oxide in the course of which propylene oxide is separated from methanol wherein this separation has the above-mentioned advantages thus rendering the process for producing propylene oxide energetically and also with respect to the purity of the distillation fractions advantageous over the prior art.

SUMMARY OF THE INVENTION

The present invention provides a method of separating propylene oxide from a mixture (M) comprising propylene oxide and methanol, said method comprising
(i) introducing said mixture (M) into an extractive distillation column;
(ii) additionally introducing an extracting solvent into said extractive distillation column;
(iii) distilling propylene oxide overhead from said extractive distillation column as top stream;
(iv) withdrawing a bottoms stream from said extractive distillation column;
(v) compressing the top stream obtained overhead in (iii) by means of at least one compressor to give a compressed vapor.

The present invention also provides a method of separating propylene oxide from a mixture (M) comprising 5 to 15 percent by weight propylene oxide, 50 to 85 percent by weight methanol, and 10 to 25 percent by weight water, said method comprising
(i) introducing said mixture (M) into an extractive distillation column;
(ii) additionally introducing a polar extracting solvent into said extractive distillation column;
(iii) distilling propylene oxide overhead from said extractive distillation column as top stream, the top stream comprising 100 ppm methanol or less;
(v) compressing the top stream obtained overhead in (iii) by means of at least one compressor to give a compressed vapor,
(vi) condensing the compressed vapor obtained in (v) and returning at least part of the heat of condensation to at least one reboiler employed in the extractive distillation column.

The present invention also provides a method of separating propylene oxide from a mixture (M) comprising 5 to 15 percent by weight propylene oxide, 50 to 85 percent by weight methanol, and 10 to 25 percent by weight water, said method comprising
(i) introducing said mixture (M) into an extractive distillation column;
(ii) additionally introducing water into said extractive distillation column in an amount of 2 percent by weight of the mixture (M) or less;
(iii) distilling propylene oxide overhead from said extractive distillation column as top stream at a pressure of from 300 to 750 mbar and a bottoms temperature of from 40 to 70° C., the top stream comprising 100 ppm methanol or less;
(iv) withdrawing a bottoms stream from said extractive distillation column comprising 100 ppm propylene oxide or less;
(v) compressing the top stream obtained overhead in (iii) to a pressure of from 2 to 4 bar by means of at least one compressor to give a compressed vapor,
(vi) condensing the compressed vapor obtained in (v) and returning at least part of the heat of condensation to at least one vaporizer employed in the extractive distillation column.

The present invention also provides a method of separating propylene oxide from a mixture (M) comprising 5 to 15 percent by weight propylene oxide, 50 to 85 percent by weight methanol, and 10 to 25 percent by weight water, said method comprising
(i) introducing said mixture (M) into an extractive distillation column;
(ii) additionally introducing water into said extractive distillation column in an amount of from 0.45 to 1 percent by weight of the mixture (M);
(iii) distilling propylene oxide overhead from said extractive distillation column at a bottoms temperature of from 50 to 60° C. and a pressure of from 450 to 500 mbar, the propylene oxide fraction comprising 50 ppm methanol or less;
(iv) withdrawing a bottoms stream from said extractive distillation column, said bottoms stream comprising 100 ppm propylene oxide or less;
(v) compressing the top stream obtained in (iii) to a pressure in the range from 2 to 4 bar by means of at least one compressor to give a compressed vapor;
(vi) condensing the compressed vapor obtained in (v) and returning at least part of the heat of condensation to at least one vaporizer used in the extractive distillation column,
(vii) cooling at least part of the condensate obtained in (vi) to a temperature in the range of from 10 to 30° C. in at least one heat exchanger and returning this part of the cooled condensate as reflux to the distillation column employed in (iii) so that the mass ratio of reflux to distillate is 4 or less;

wherein the mixture (M) is formed by reacting propene with hydrogen peroxide in methanol as solvent and in the presence of a titanium zeolite fixed-bed catalyst.

The present invention also provides a method of preparing propylene oxide, said reaction comprising reacting propene with hydrogen peroxide in methanol as solvent and in the presence of a titanium zeolite fixed-bed catalyst, said reaction resulting in mixture (M) comprising 5 to 15 percent by weight propylene oxide, 50 to 85 percent by weight methanol, and 10 to 25 percent by weight water, or a mixture being worked up to give mixture (M), said method further comprising
(i) introducing said mixture (M) into an extractive distillation column;
(ii) additionally introducing water into said extractive distillation column in an amount of 0.45 to 1 percent by weight of the mixture (M);
(iii) distilling propylene oxide overhead from said extractive distillation column as top stream at a pressure of from 450 to 500 mbar and a bottoms temperature of from 50 to 60° C., the top stream comprising 100 ppm methanol or less;
(iv) withdrawing a bottoms stream from said extractive distillation column and using the energy stored in the bottom stream at least partly for heating the mixture (M) before said mixture is introduced into the extractive distillation column in (i);
(v) compressing the top stream obtained overhead in (iii) to a pressure of from 2.5 to 3.5 bar by means of at least one compressor to give a compressed vapor,
(vi) condensing the compressed vapor obtained in (v) and returning at least part of the heat of condensation to at least one vaporizer employed in the extractive distillation column,
(vii) cooling at least part of the condensate obtained in (vi) to a temperature in the range from 10 to 30° C. in at least one heat exchanger and returning this part of the cooled condensate as reflux to the extractive distillation column used in (iii) in an amount so that the mass ratio of reflux to distillate is 4 or less;

(viii) depressurizing a compressed propene stream into the at least one heat exchanger in (vii), vaporizing the propene stream in the at least one heat exchanger and subsequently using the propene as reactant in said reaction.

BRIEF DESCRIPTION OF THE DRAWINGS

The accompanying

DETAILED DESCRIPTION OF THE INVENTION

Figure 1:
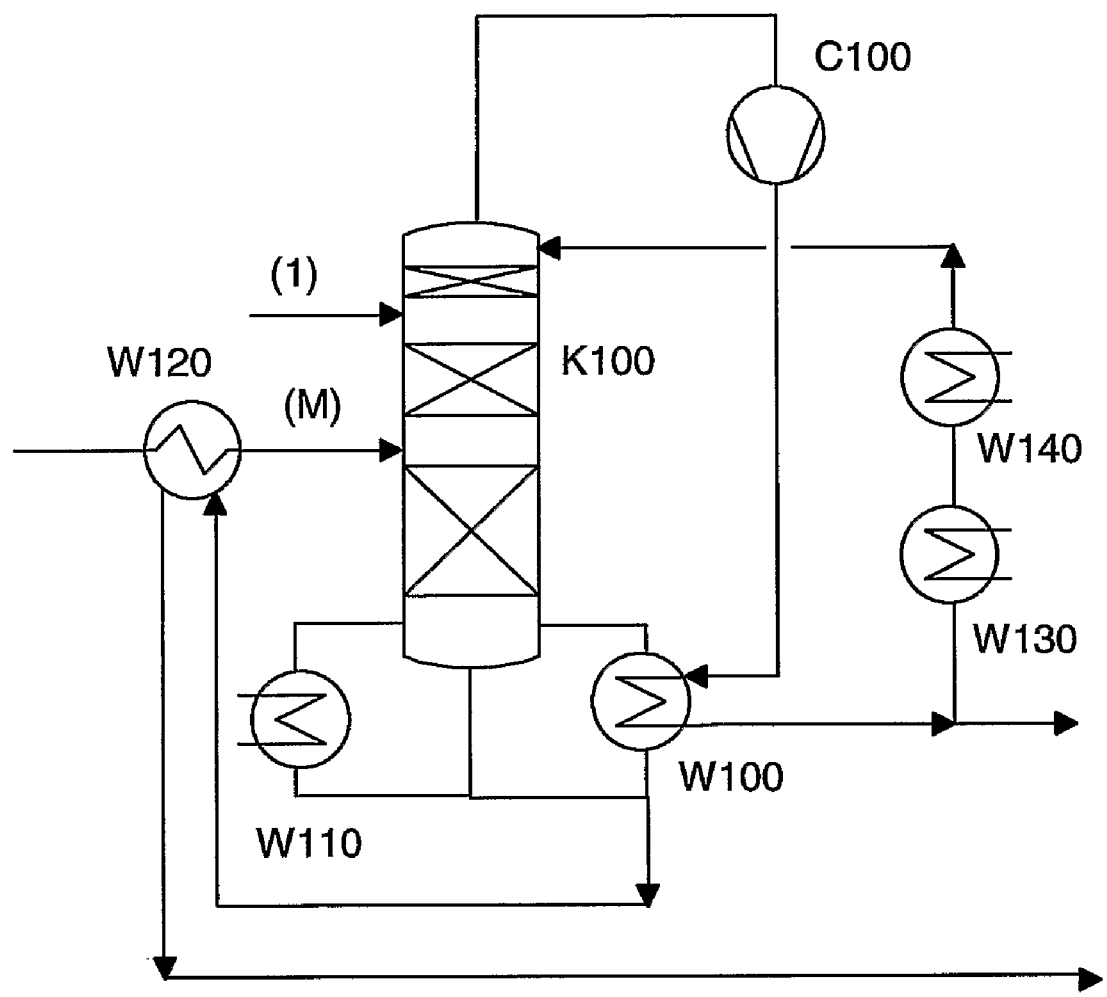
FIG. 1 provides a diagram showing a preferred embodiment of the present invention, FIG. 2 provides a diagram showing another preferred embodiment of the present invention, FIG. 3 provides a diagram showing a process of the prior art, FIG. 4 provides a diagram showing another process of the prior art, FIG. 5 provides a diagram showing yet another process of the prior art.

According to the present invention, propylene oxide is separated from a mixture (M) which comprises propylene oxide and methanol. Preferred mixtures (M) used in the present invention comprise up to 50, more preferably from 1 to 50, more preferably from 2 to 45, more preferably from 3 to 35, more preferably from 4 to 25 and still more preferably from 5 to 15 percent of weight propylene oxide. Especially preferred mixtures (M) comprise from 6 to 12 percent by weight and particularly preferably from 8 to 10.5 percent by weight of propylene oxide. Furthermore, preferred mixtures (M) used in the present invention comprise up to 99, more preferably up to 95, more preferably up to 90 and still more preferably up to 85 percent by weight of methanol, and at least 10, more preferably at least 20, more preferably at least 30, more preferably at least 40 and especially preferably at least 50 percent by weight of methanol. Especially preferred mixtures (M) therefore comprise from 40 to 90, more preferably from 50 to 85 percent by weight of methanol. Particularly preferred mixtures (M) comprise from 55 to 85 percent by weight, preferably from 60 to 80 percent by weight and particularly preferably from 65 to 75 percent by weight of methanol. Thus, preferred mixtures (M) used according to the present invention comprise 5 to 50 percent by weight of propylene oxide and 50 to 85 percent by weight of methanol, based on the total weight of mixture (M).

With regard to the method of the invention, mixture (M) may comprise one or more additional compounds. As to these compounds, no specific restrictions exist on the condition that propylene oxide can be distilled overhead from the extractive distillation column so as to separate propylene oxide from the methanol comprised in (M).

According to a preferred embodiment, the mixture (M) additionally comprises water, more preferably water in amount of up to 25, more preferably from 1 to 25, more preferably from 2 to 25, more preferably from 3 to 25, more preferably from 4 to 25, more preferably from 5 to 25, more preferably from 6 to 25, more preferably from 7 to 25, more preferably from 8 to 25, more preferably from 9 to 25 and still more preferably from 10 to 25 percent by weight of water, based on the total weight of mixture (M). Therefore, the mixture (M) for example may comprise from 10 to 25 or from 10 to 20 or from 10 to 15 or from 15 to 25 or from 15 to 20 or from 20 to 25 percent by weight water, based on the total weight of mixture (M).

According to a preferred embodiment where (M) comprises from 10 to 25 percent by weight of water, (M) preferably comprises from 5 to 45, more preferably from 5 to 40, more preferably from 5 to 35, more preferably from 5 to 30, more preferably from 5 to 25, more preferably from 5 to 20 and still more preferably from 5 to 15 percent by weight of propylene oxide, based on the total weight of mixture (M).

Therefore, the present invention also provides a method as described above wherein the mixture (M) comprises form 50 to 85 percent by weight methanol, from 5 to 15 percent by weight propylene oxide, from 10 to 25 percent by weight water, based on the total weight of the mixture (M).

In addition to methanol and propene and, preferably, water, the mixture (M) may comprise at least one further compound.

According to a preferred embodiment of the present invention, the mixture (M) directly or indirectly results from a process where propylene oxide is prepared by reacting propene with a hydroperoxide in the presence of methanol as solvent. Therefore, the mixture (M) may additionally comprise unreacted propene and/or unreacted hydroperoxide and/or at least one by-product of said epoxidation reaction such as propylene glycol and/or acetaldehyde.

The reaction mixture obtained from said epoxidation reaction may be directly introduced in (i) as mixture (M) if the content of (M) regarding methanol, propylene oxide and preferably water is within above-mentioned ranges.

According to an especially preferred embodiment of the present invention, the reaction mixture obtained from said epoxidation reaction is worked up prior to the introduction in (i) of the inventive method. Working up the reaction mixture obtained from said epoxidation reaction may be carried out in each conceivable way on the condition that a mixture (M) is obtained which may be introduced in (i). Said work up may comprise the separation and/or the addition of at least one compound from and/or to the mixture obtained from the epoxidation reaction. Preferably, at least one compound is separated from the mixture obtained from the epoxidation reaction.

According to an even more preferred embodiment of the present invention, at least one compound is separated from the mixture obtained from the epoxidation reaction, said at least one compound having a lower boiling point than propylene oxide, methanol and water.

Depending on the reaction conditions applied and the reactants used for the epoxidation reaction, these low boilers may be, for example, unreacted propene and/or propane which can be introduced in the epoxidation reaction in case, e.g., chemical grade propene is used as reactant having a volume ratio of propene:propane of from about 99.5:0.5 to 94:6.

According to a still further preferred embodiment of the present invention, unreacted propene is separated from the reaction mixture obtained from the epoxidation reaction in at least one distillation column, and the high boiling fraction whose respective content regarding methanol, propylene oxide and water are within the above-mentioned ranges is introduced as (M) in (i) of the method of the present invention.

Therefore, the present invention also provides a method of preparing propylene oxide, said reaction comprising reacting propene with a hydroperoxide in methanol as solvent, said reaction resulting in a mixture (M) comprising 5 to 15 percent by weight propylene oxide, 50 to 85 percent by weight methanol, and 10 to 25 percent by weight water, or preferably resulting in a mixture comprising propylene oxide, methanol, water, unreacted propene and optionally propane, said mixture being worked up to give said mixture (M) comprising 5 to 15 percent by weight propylene oxide, 50 to 85 percent by weight methanol, and 10 to 25 percent by weight water, and said mixture being further subjected to at least steps (i) to (v) as described hereinabove and hereinunder. According to this embodiment of the present invention, working up preferably comprises separating propene and, if present, preferably also propane by distillation so as to give a mixture (M), preferably comprising not more than 500 ppm, preferably not more than 400 ppm and especially preferably not more than 350 ppm of propene and comprising not more than 50 ppm, preferably not more than 25 ppm and especially preferably not more than 10 ppm of propane, and preferably not more than 200 ppm, more preferably not more than 150 ppm and especially preferably not more than 100 ppm of acetaldehyde. Accordingly, a mixture (M) is obtained comprising especially preferably not more than 350 ppm of propene and not more than 10 ppm of propane and not more than 100 ppm of acetaldehyde.

According to a further embodiment of the present invention, the mixture (M) introduced in (i) comprises not more than 1 percent by weight, more preferably not more than 0.75 percent by weight and especially preferably not more than 0.65 percent by weight of high boiling compounds such as methoxypropanols and/or hydroperoxide and/or propylene glycols.

In the context of the present invention, the term "hydroperoxide" refers to a compound of the formula ROOH. Details regarding the preparation of hydroperoxides and regarding hydroperoxides which can be used, inter alia, in the method of the present invention may be found in DE-A-198 35 907 the respective content of which is incorporated in the context of the present invention by reference. Examples of hydroperoxides which can be used for the purposes of the present invention are, inter alia, tert-butyl hydroperoxide, ethylbenzene hydroperoxide, tert-amyl hydroperoxide, cumene hydroperoxide, cyclohexyl hydroperoxide, methylcyclohexyl hydroperoxide, tetrahydronaphthalene hydroperoxide, isobutylbenzene hydroperoxide, ethylnaphthalene hydroperoxide, peracids such as peracetic acid and hydrogen peroxide. Mixtures of two or more hydroperoxides can also be used according to the present invention. Preference is given to using hydrogen peroxide as hydroperoxide in the method of the present invention, and further preference is given to using an aqueous hydrogen peroxide solution. Most preferably, the aqueous hydrogen peroxide solution comprises hydrogen peroxide in a concentration in the range of from 1 to 90, more preferably of from 10 to 70 and especially preferably of from 30 to 50 wt.-%, based on the total weight of the solution. It is also possible to use a mixture of two or more different hydroperoxides.

The epoxidation reaction the mixture (M) directly or indirectly is obtained from may be carried out in the presence of each suitable catalyst or a suitable combination of two or more catalysts. Particularly preferred, a zeolite containing titanium is employed, wherein zeolites known to the person skilled in the art as "titanium silicalites" (TS) are particularly preferred. Such zeolites containing titanium, in particular those having a crystalline structure of the MFI-type as well as ways for producing them are described, for example, in WO 98/55228, EP-A-0 311 983, or EP-A-0 405 978. The respective content of these documents is hereby incorporated by reference. In addition to Si and Ti, said zeolite materials may contain additional elements, such as aluminum, zirconium, tin, iron, cobalt, nickel, gallium, boron, or small amounts of fluorine. It is possible that the titanium of the zeolite is partly or completely replaced by vanadium, zirconium, or niobium, or any mixture of two or more of these components. Zeolites containing titanium and having a MFI-structure are known to yield a characteristic pattern in x-ray diffraction. Furthermore, these materials display a vibration band in the infrared (IR) at approximately 960 $cm^{-1}$. Therefore, it is possible to distinguish the zeolites containing titanium from crystalline or amorphous $TiO_2$-phases or from alkaline metal titanates. In a further preferred embodiment, the at least one zeolite catalyst comprises at least one of the elements titanium, germanium, tellurium, vanadium, chromium, niobium, zirconium. Particularly preferred are zeolite catalysts having a pentasil zeolite structure, in particular the structural types that can be, via X-ray diffraction, assigned to the structure types of ABW-, ACO-, AEI-, AEL-, AEN-, AET-, AFG-, AFI-, AFN-, AFO-, AFR-, AFS-, AFT-, AFX-, AFY-, AHT-, ANA-, APC-, APD-, AST-, ATN-, ATO-, ATS-, ATT-, ATV-, AWO-, AWW-, BEA-, BIK-, BOG-, BPH-, BRE-, CAN-, CAS-, CFI-, CGF-, CGS-, CHA-, CHI-, CLO-, CON-, CZP-, DAC-, DDR-, DFO-, DFT-, DOH-, DON-, EAB-, EDI-, EMT-, EPI-, ERI-, ESV-, EUO-, FAU-, FER-, GIS-, GME-, GOO-, HEU-, IFR-, ISV-, ITE-, JBW-, KFI-, LAU-, LEV-, LIO-, LOS-, LOV-, LTA-, LTL-, LTN-, MAZ-, MEI-, MEL-, MEP-, MER-, MFI-, MFS-, MON-, MOR-, MSO-, MTF-, MTN-, MTT-, MTW-, MWW-, NAT-, NES-, NON-, OFF-, OSI-, PAR-, PAU-, PHI-, RHO-, RON-, RSN-, RTE-, RTH-, RUT-, SAO-, SAT-, SBE-, SBS-, SBT-, SFF-, SGT-, SOD-, STF-, STI-, STT-, TER-, THO-, TON-, TSC-, VET-, VFI-, VNI-, VSV-, WIE-, WEN-, YUG-, ZON, as well as mixed structures of at least two or more of the aforementioned structures. Furthermore, it is conceivable to use zeolite catalysts containing titanium with the structure of ITQ-4, ITQ-9, SSZ-24, TTM-1, UTD-1, CIT-1 or CIT-5. Furthermore zeolites containing titanium are such of the structure types ZSM-48 or ZSM-12. Zeolites containing titanium of the structure MFI, MEL or MFI/MEL mixed structures, as well as MWW, BEA or mixed structures thereof are preferred in the context of the present invention. In the context of the present invention, zeolite catalysts containing titanium that are referred to, in general, as "TS-1", "TS-2" or "TS-3", as well as zeolites containing titanium displaying a structure that is isomorphous to zeolite beta are further preferred.

Although it is possible to carry out the reaction using a suspension catalyst, particular preference is given to a heterogeneous catalyst and still more preferably a fixed-bed catalyst. Therefore, according to this preferred embodiment of the present invention, it is not necessary to separate the catalyst from the reaction mixture obtained from the epoxidation reaction.

Therefore, the present invention also provides a method of separating propylene oxide from a mixture (M) comprising propylene oxide, methanol and preferably water, as described above, wherein the mixture (M) is directly or indirectly, after at least one work up step, obtained from an epoxidation process wherein propene is reacted with a hydroperoxide, preferably hydrogen peroxide, in the presence of methanol as solvent and in the presence of a fixed-bed catalyst, preferably a fixed-bed zeolite catalyst, more preferably a fixed-bed titanium zeolite catalyst, still more preferably a fixed-bed TS-1 type titanium silicalite catalyst, and wherein said catalyst does not have to be separated from the reaction mixture resulting from the epoxidation process.

Accordingly, the present invention also provides a method of preparing propylene oxide, said reaction comprising reacting propene with a hydroperoxide, preferably hydrogen peroxide, in methanol as solvent, said reaction resulting in a mixture (M) comprising 5 to 15 percent by weight propylene oxide, 50 to 85 percent by weight methanol, and 10 to 25 percent by weight water, or preferably resulting in a mixture comprising propylene oxide, methanol, water, unreacted propene and optionally propane, said mixture being worked up to give said mixture (M) comprising 5 to 15 percent by weight propylene oxide, 50 to 85 percent by weight methanol, and 10 to 25 percent by weight water, and said mixture being further subjected to at least steps (i) to (v) as described hereinabove and hereinunder, wherein the epoxidation is carried out in the presence of a fixed-bed catalyst, preferably a fixed-bed zeolite catalyst, more preferably a fixed-bed titanium zeolite catalyst, still more preferably a fixed-bed TS-1 type titanium silicalite catalyst, and wherein said catalyst does not have to be separated from the reaction mixture resulting from the epoxidation process.

In (i) of the present invention, any suitable extractive distillation column may be used. Preferably, the column has up to 80 theoretical plates such as from 10 to 80 or from 20 to 80 or from 30 to 80 or from 40 to 80 of from 50 to 80 or from 60 to 80 or preferably from 60 to 65 or from more than 60 to 80 such as from 61 to 80 or from 65 to 80 or from 70 to 80 or from 75 to 80. Preferably, the column has more than 60 theoretical plates such as from 61 to 65 theoretical plates. Two or more columns may be used according to the present invention wherein two or more columns may be connected in series and/or two or more columns may be arranged in parallel. Preferably, one column is used.

According to (ii) of the present invention, at least one extracting solvent is added. As to the chemical nature of the at least one extracting solvent, no specific limitations exist on the condition that extractive distillation is possible according to (iii). As extracting solvents, non-polar and/or polar solvents are possible. As non-polar solvents, hydrocarbons such as hydrocarbons having up to 16 carbon atoms such as hydrocarbons from 6 to 16 carbon atoms are preferred. Possible hydrocarbons comprise, for example, from 12 to 16, preferably from 13 to 15 carbon atoms or from 6 to 12 or from 6 to 11 or from 6 to 10 or from 7 to 9 carbon atoms. Mixtures of two or more of above-mentioned hydrocarbons are possible, such as mixtures of hydrocarbons having 7, 8 and 9 carbon atoms or mixtures of hydrocarbons having 13, 14 and 15 carbon atoms. According to an especially preferred embodiment of the present invention, the at least one extracting solvent is a polar solvent or a mixture of at least one polar solvent and at least one non-polar solvent. According to a particularly preferred embodiment of the present invention, the at least one extracting solvent is a polar solvent.

Therefore, the present invention also provides a method of separating propylene oxide from a mixture (M), as described above, wherein in (ii), at least one polar solvent is added. As to the chemical nature of the at least one polar solvent, no specific limitations exist on the condition that extractive distillation can be carried out according to (iii).

Preferred polar solvents are water, alcohols having one or more hydroxy groups such as one, two, three or more hydroxy groups, preferably monools and diols, or ethers, preferably ether compounds having at least one hydroxy group, preferably one hydroxy group such as 1-methoxy-2-propanol and/or 2-methoxy-1-propanol. Especially preferred is water. Especially preferred is water wherein, for example, demineralized water, potable water, suitable industrial water, suitable waste water, especially suitably treated waste water, suitable process water or a mixture of two or more thereof can be used. The water introduced in the process of the present invention should be essentially free of organic material, especially essentially free of methanol. According to one embodiment of the present invention, the water introduced in (ii) is a process water from a suitable process such as a process carried out in the epoxidation plant in which the method of the present invention is conducted. According to one aspect of the present invention, the process water is taken from a process in the epoxidation plant where methanol as solvent of the epoxidation reaction and water are separated from each other. Preferably, the water is taken from the bottom of at least one distillation column in which methanol as solvent of the epoxidation reaction and water are separated. More preferably, the water resulting from said separation process, optionally after one or more additional purification steps, is introduced in (ii), and the methanol resulting from said separation process, optionally after one or more additional purification steps, is recirculated as solvent into the epoxidation reaction. Thus, the present invention also describes a method as described above wherein an integrated process is implemented by working up a mixture comprising methanol and water by separating methanol and water from each other, and by recirculating the separated water, optionally after one or more additional purification steps, preferably without any additional purification steps, into (ii), and optionally recirculating the separated methanol, optionally after one or more additional purification steps, as solvent into the epoxidation reaction from which the mixture (M) introduced in (i) results.

Therefore, the present invention also provides a method of separating propylene oxide from a mixture (M) as described above wherein water is introduced as polar solvent into said extractive distillation column in (ii).

According to an even more preferred embodiment, no other solvent except water is introduced as polar solvent in (ii). According to another preferred embodiment, as mentioned above, no propylene glycol is used as polar solvent.

The preferred embodiment according to which water and no propylene glycol is used as polar solvent, shows, among others, the advantages that water is cheaply available compared to propylene glycol and can be discarded without having disadvantageous ecological impacts. Therefore, in case propylene glycol is used as polar solvent, working up and recirculating the propylene glycol is necessary in order to render the process ecologically and economically efficient. However, working up necessarily includes at least one additional process step which is superfluous in case water is used as polar solvent.

According to a preferred embodiment of the present invention, the at least one polar solvent is introduced in the extractive distillation column about 15 theoretical plates, more preferably about 10 theoretical plates below the upper end of the extractive distillation column.

The at least one solvent, preferably water, may be introduced in the column as liquid or as vapor or as liquid as well as vapor. If two or more solvents are used, at least one solvent may be introduced as liquid and at least one other solvent may be introduced as vapor.

According to a preferred embodiment, water is used as polar solvent and introduced in the extractive distillation column as liquid and/or as vapor. If water is introduced as vapor, the vapor introduced in (ii) has a pressure of not more than 2 bar, more preferably of not more than 1 bar, more preferably not more than 900 mbar and especially preferably not more than 800 bar.

As far as the amount of solvent, preferably polar solvent introduced in the extractive distillation column according to (ii) is concerned, no specific limitations exist. Preferably, solvent, more preferably polar solvent, and in particular water, is introduced in an amount of not more than 2 percent by weight, based on the weight of the mixture (M). More preferably, solvent, still more preferably the polar solvent is introduced in an amount of not more than 1.8, more preferably not more than 1.6, more preferably not more than 1.4, more preferably not more than 1.2 and still more preferably not more than 1 percent by weight, based on the weight of the mixture (M). Further preferred are amounts of polar solvent of at least 0.2, more preferably at least 0.25, more preferably at least 0.3 and still more preferably at least 0.4 percent by weight, based on the weight of the mixture (M). Therefore, preferred ranges are, for example, from 0.2 to 2, more preferably from 0.3 to 1.6, more preferably from 0.4 to 1.2, and still more preferably from 0.45 to 1 percent by weight, based on the weight of the mixture (M).

Therefore, the present invention also provides a method of separating propylene oxide from a mixture (M), as described above, wherein in (ii), at least one polar solvent, in particular water, preferably as vapor at a pressure of not more than 2 bar, is introduced in an amount of from 0.45 to 1 percent by weight, based on the weight of the mixture (M).

Preferred mass ratios of propylene oxide comprised in (M): extracting solvent added in (ii) are from 0.6:1 to 70:1, more preferably from 1:1 to 20:1 and especially preferably from 3:1 to 8:1 such as, for example, from 4:1 to 7:1 or from 5:1 to 7:1 or from 6:1 to 7:1.

Distillation in (iii) is preferably carried out at pressures of 1.5 bar or less, more preferably of 1.4 bar or less, more preferably of 1.2 bar or less, more preferably of 1.1 bar or less and especially preferably at a pressure of 1.013 bar or less, and still more preferably under reduced pressure. For the purposes of the present invention, the term "distillation under reduced pressure" refers to any distillation which is carried out at a pressure of less than 1.013 bar. The distillation in (iii) is therefore preferably carried out at pressures in a range of up to 1 bar, more preferably in a range from 300 to 950 mbar, more preferably from 300 to 900 mbar, more preferably from 300 to 850 mbar, more preferably from 300 to 800 mbar and particularly preferably in a range from 300 to 750 mbar. Other preferred ranges of the pressure at which distillation is carried out are from 300 to 700, more preferably from 300 to 650, more preferably from 300 to 600, more preferably from 300 to 550 and still more preferably from 300 to 500 mbar, or from 350 to 750, more preferably from 400 to 750, more preferably from 450 to 750, more preferably from 450 to 700, more preferably from 450 to 650, more preferably from 450 to 600, more preferably from 450 to 550 and especially preferably from 450 to 500 mbar.

Therefore, the present invention also provides a method of separating propylene oxide from a mixture (M) as described above, wherein in (iii), distillation is carried out at a pressure of from 300 to 750, more preferably of from 300 to 500 and especially preferably of from 450 to 500 mbar.

The term "pressure at which the distillation is carried out" as used in the context of the present invention relates to the pressure at the top of the column in which the distillation is carried out.

The bottoms temperature of the extractive distillation column generally depends on the pressure at which distillation is carried out. Preferably, the bottoms temperature according to the present invention is below 90° C., more preferably not more than 85° C., more preferably not more than 80° C., more preferably not more than 75° C., more preferably not more than 70° C., more preferably not more than 65° C. and especially preferably not more than 60° C. Especially preferred bottoms temperatures of the extractive distillation are for example from 40 to 70° C. or from 40 to 65° C. or from 40 to 60° C. or from 45 to 70° C. or from 45 to 65° C. or from 45 to 60° C. or from 50 to 70° C. or from 50 to 65° C. or from 50 to 60° C.

Therefore, the present invention also provides a method of separating propylene oxide from a mixture (M) as described above, wherein in (iii), distillation is carried out bottoms temperatures in the range of from 30 to 80, more preferably from 40 to 70, more preferably from 45 to 70, more preferably from 45 to 65 and especially preferably from 50 to 60° C.

Especially preferred combinations of pressure ranges and bottoms temperature ranges are for example from 300 to 750 mbar and from 40 to 70° C. or from 300 to 500 mbar and from 40 to 60° C. or from 450 to 500 mbar and from 50 to 60° C.

Therefore, the present invention also provides a method of separating propylene oxide from a mixture (M) as described above, wherein in (iii), distillation is carried out at a pressure of from 300 to 500 mbar and at a temperature of from 40 to 60° C., more preferably at a pressure of from 450 to 500 mbar and at a temperature of from 50 to 60° C.

Therefore, the present invention provides a method of separating propylene oxide from a mixture (M) by extractive distillation, preferably using water as extracting solvent in an amount of not more than 2 percent by weight based on the weight of (M), wherein the extractive distillation is carried out at low pressures of 750 mbar and below, preferably from 300 to 750 mbar, more preferably from 300 to 500 mbar and especially preferably from 450 to 500 mbar, and simultaneously at low temperatures of 70° C. and below, preferably from 40 to 70° C., more preferably from 40 to 60° C. and still more preferably from 50 to 60° C. such as at about 51, 52, 53, 54, 55, 56, 57, 58 or 59° C.

As extractive distillation column, it is essentially possible to use any column. Particular preference is given to a distillation column configured as a packed column, more preferably a packed column containing ordered packing. Such a packed column has a high separation efficiency per meter of packing and displays only a very small pressure drop. While the ordered packing mentioned can essentially be of any type, preference is given to packing which has a specific surface area in the range from 100 to 750 $m^2/m^3$. It is possible to use sheet metal packing, for example from Montz (type B1 100 to B1 500) or from Sulzer ChemTech (Mellapak 125 to Mellapak 750), or mesh packing from Montz (type A3 500 to A3 750) or from Sulzer ChemTech (type BX or CY). The unit $m^2/m^3$ refers to the geometric surface area of the material forming the packing per cubic meter of packing.

According to the present invention, the propylene oxide fraction separated from methanol and water is preferably distilled overhead.

The propylene oxide fraction distilled overhead in (iii) preferably comprises at least 99.0, more preferably at least 99.5, more preferably at least 99.6 and still more preferably at least 99.7 percent by weight propylene oxide, based on the total weight of the propylene oxide fraction.

The propylene oxide fraction distilled overhead in (iii) preferably comprises not more than 500 ppm, more preferably not more than 200 ppm, more preferably not more than 100 ppm, more preferably not more than 50 ppm, more preferably not more than 20 ppm and still more preferably not more than 10 ppm of methanol, based on the total weight of the propylene oxide fraction.

The propylene oxide fraction distilled overhead in (iii) preferably comprises not more than 200 ppm, more preferably not more than 100 ppm, more preferably not more than 75 ppm, more preferably not more than 60 ppm, and still more preferably not more than 20 ppm of water, based on the total weight of the propylene oxide fraction.

The propylene oxide fraction distilled overhead in (iii) preferably comprises not more than 0.5, more preferably not more than 0.3, and still more preferably not more than 0.25 percent by weight of propene and propane, based on the total weight of the propylene oxide fraction.

At the extractive distillation conditions according to the present invention, the high boiler fraction withdrawn in (iv) as bottoms stream comprises, in addition to water and methanol, not more than 100 ppm, preferably not more than 75 and especially preferably not more than 50 ppm of propylene oxide, based on the weight of the high boiler fraction.

At the extractive distillation conditions according to the present invention where no propylene glycol but preferably water is used as extracting polar solvent in (ii), the high boiler fraction withdrawn in (iv) as bottoms stream comprises, in addition to water and methanol, not more than 1, preferably not more than 0.5 and especially preferably not more than 0.2 percent by weight of propylene glycol, based on the weight of the high boiler fraction.

In step (v) of the method of the present invention, the vapor top stream obtained at the top of the extractive distillation column and consisting essentially of propylene oxide, is compressed. This compression can generally be carried out using any suitable methods. In particular, the vapor can be compressed mechanically or thermally, and the compression can be carried out in one or more apparatuses. It is thus possible to compress the vapor mechanically in at least one compression apparatus or to compress the vapor thermally in at least one compression apparatus or firstly to compress the vapor mechanically in at least one compression apparatus and then to compress the vapor thermally in at least one compression apparatus or firstly to compress the vapor thermally in at least one compression apparatus and then to compress the vapor mechanically in at least one compression apparatus.

Apparatuses suitable for mechanical compression are, for instance, rotary piston compressors, screw compressors, turbocompressors having an axial or radial construction, diaphragm-type compressors or blowers. For the purposes of the present invention, compression can be carried out using one of these apparatuses or a combination of two or more of these apparatuses, with each of the compressors used being able to have one or more stages.

An example of an apparatus for thermal compression is a steam ejector which can be equipped with a fixed or regulatable driving nozzle.

For the purposes of the present invention, the vapor is particularly preferably compressed mechanically and particularly preferably in a single apparatus and still more preferably mechanically in a single apparatus. Preference is given to a turbocompressor. According to preferred embodiments of the present invention, the compression is carried out in the single apparatus, more preferably the turbocompressor, in one or more stages such as in a single stage or in two stages or in three stages.

Accordingly, the present invention also provides a method of separating propylene oxide from a mixture (M) as described above wherein compression of the vapor is carried out using a turbocompressor.

According to a preferred embodiment of the present invention, where distillation in (iii) is carried out at a pressure of 1.5 bar or less, the vapor is compressed in (iv) by means of the preferred mechanical compressor so that the vapor has a pressure of generally of more than 1.5 bar, more preferably from more than 1.5 to 5 bar, more preferably from 2 to 4 bar and particularly preferably from 2.5 to 3.5 bar, after leaving the compressor.

Therefore, the present invention also provides a method of separating propylene oxide from a mixture (M) as described above wherein, in (iii), the distillation is carried out at a pressure of 1.5 bar or less, and, in (v), the top stream is compressed to a pressure of more than 1.5 bar.

In general, the vapor is brought by compression to a temperature which is at least 1° C. higher than the temperature of the medium vaporizing in the bottom of the distillation column. The vapor is preferably brought by compression to a temperature which is from 2 to 40° C., more preferably from 5 to 30° C. and particularly preferably from 10 to 25° C., higher than the temperature of the medium vaporizing in the distillation column. Typical temperatures of the compressed vapor are in the range of from 58 to 100° C., more preferably from 65 to 95° C. and especially preferably from 70 to 90° C.

Accordingly, the present invention also provides a method of separating propylene oxide from a mixture (M) as described above wherein the vapor obtained as top stream from the extractive distillation column is compressed to a pressure in the range from 2 to 4 bar in (v) and the compressed vapor has a temperature which is from 10 to 25° C. above the temperature of the medium vaporizing in the extractive distillation column in (iii).

As a result of the compression step according to the present invention, the method of the present invention makes possible the above-described favorable pressure range below 1.013 bar, preferably the range from 300 to 750 mbar, for the extractive distillation without having to accept the disadvantage of a low condensation temperature and the high refrigeration power which then has to be made available.

Therefore, the present invention also provides a method of separating propylene oxide from a mixture (M) as described above wherein in (iii), the distillation is carried out at a pressure of from 300 to 750 mbar and a bottoms temperature of from 40 to 70° C., and, in (v), the top stream is compressed to a pressure of from 2 to 4 bar.

Depending on the specific composition of the mixture (M) and the required purity of the propylene oxide fraction in respect of the residual concentration of solvent, preferably methanol, the compressor power is typically in the range of from 3.5 to 8 MW. The corresponding condensation/refrigeration power which would have to be employed at a temperature of the compressed vapor in the range from 12 to 20° C. in a process of the prior art where the top stream is not compressed, would have been in a typical range of from 15 to 30 MW.

The energy additionally stored in the vapor as a result of compression can, for example, preferably be fed to any process, with recirculation into the method of the present invention being especially preferred. In general, all or part of the stored energy can be introduced into any method step. Particular preference is given to recirculation of at least part of the energy stored in the compressed vapor to the distillation step (iii). Particular preference is in this case given to at least one vaporizer of the distillation column, for example at least one intermediate vaporizer or the main vaporizer or at least one intermediate vaporizer and the main vaporizer, being operated by means of the energy stored in the compressed vapor. In this way, a heat pump is realized in the method of the present invention as a result of this integrated operation of the method rendering the overall process energetically highly advantageous.

Depending on the amount of energy which shall be withdrawn from the compressed vapor stream and be used further, for example for providing the heat pump described hereinabove, it might be necessary to divide the compressed vapor stream and use only a part of said stream for realizing the heat pump. According to a preferred embodiment of the present invention, the other part of the stream is cooled in at least one further heat exchanger. According to a still further preferred embodiment, the cooled stream leaving this heat exchanger is combined with the stream leaving the heat exchanger which is used for the preferably realized heat pump as described hereinabove, and the combined streams may be further used as described hereinunder, as discussed, for example, with regard to step (vii) of the present invention.

In a very particularly preferred embodiment, the compressed gaseous vapor is liquefied in at least one condenser and the heat of condensation is at least partly used for operating at least one of the abovementioned vaporizers. Particular preference is given to the operation of the main vaporizer of the distillation column used in (iii).

Accordingly, the present invention also provides a method as described above which additionally comprises (vi) condensing the compressed vapor obtained in (v) and returning at least part of the heat of condensation to at least one reboiler employed in the extractive distillation column.

The condensation in (vi) is carried out in a vaporizer which can have essentially any configuration. Examples of embodiments of vaporizers are natural convection vaporizers, forced circulation vaporizers or falling film vaporizers. For the purposes of the present invention, preference is given to using a vaporizer which is configured as a natural convection vaporizer.

The condensate leaving the condenser or condensers of (vi) has, in the method of the present invention, a temperature of preferably from 40 to 75° C., more preferably from 45 to 70° C. and particularly preferably from 45 to 65° C.

In a preferred embodiment of the method of the present invention, at least part of the condensate obtained in (vi) is cooled further in at least one further heat exchanger so as to obtain energy which can be passed to any other process or preferably be recirculated within the method of the present invention.

This part of the condensate is preferably cooled in the further heat exchanger or exchangers to a temperature preferably in the range from 10 to 30° C., particularly preferably in the range from 12 to 20° C. This cooling step, preferably the cooling step carried out in at least one heat exchanger, can be conducted in at least one stage such as in one stage, two stages, three stages or more than three stages. The cooling step is especially preferably carried in two stages where, in the first stage, cooling is achieved by using suitable cooling water and cooling in the second stage is achieved with suitably chilled water.

In a very particularly preferred embodiment, the cooled condensate leaving this heat exchanger or exchangers is recirculated as reflux to the extractive distillation column used in (iii). According to an especially preferred embodiment of the present invention, the cooled condensate is partially refluxed into the extractive distillation column. According to an even more preferred embodiment, the mass ratio of reflux:distillate is smaller than 5, more preferably smaller than or equal to 4.9, more preferably smaller than or equal to 4.8, more preferably smaller than or equal to 4.7, and especially preferably smaller than or equal to 4 such as about 3.5 or about 3.6 or about 3.7 or about 3.8 or about 3.9 or 4.

Therefore, the present invention also provides a method of separating propylene oxide from a mixture (M) as described above, wherein the distillate obtained overhead from (iii) is partially refluxed into said extractive distillation column and wherein the ratio of reflux to distillate is smaller than or equal to 4.9.

Thus, the extractive distillation process of the present invention combines the advantages of low distillation pressures, low distillation temperatures and, simultaneously, a low reflux:distillate mass ratio.

Accordingly, the present invention also provides a method as described above which additionally comprises (vii) cooling at least part of the condensate obtained in (vi) to a temperature in the range from 10 to 30° C. in at least one heat exchanger and returning this part of the cooled condensate as reflux to the distillation column used in (iii).

In the method of the present invention, the refrigeration power employed in the heat exchanger of (vii) for cooling the condensate is preferably provided by at least a part of the method of the present invention. For example, it is conceivable for the refrigeration power required in the heat exchanger of (vii) to be taken from a refrigerant which, at another point of the method, takes up the quantity of cold withdrawn in this way. However, it is also conceivable for the refrigeration power taken up in the heat exchanger to be transferred directly from a material or mixture which can generally be in any possible state of matter. For example, preference is given, in the method of the present invention, to depressurizing a compressed stream into a compartment of the heat exchanger and at least partly, preferably completely, vaporizing it and transferring the resulting refrigeration power to the condensate present in another compartment of the heat exchanger. Preference is in turn given to an embodiment in which this compressed stream is a compressed propene stream. In particular, this propene stream is a compressed propene stream which is firstly, as described above, depressurized into the heat exchanger and vaporized in the heat exchanger and is subsequently used as reactant in the preferred epoxidation reaction the mixture (M) directly or indirectly results from.

The compressed propene stream is particularly preferably vaporized completely in the vaporizer or vaporizers used in (vii).

Accordingly, the present invention also provides a method of separating propylene oxide from a mixture (M) as described above wherein the propene compressed in the vaporizer or vaporizers used in (vii) is vaporized completely with depressurization.

For example, the propene stream has preferably been compressed to a pressure in the range from 20 to 35 bar at a temperature in the range from 5 to 30° C., preferably from 10 to 30° C., more preferably from 15 to 30° C. and particularly preferably from 20 to 30° C., and is, according to the present invention depressurized in step (vii) to a pressure in the range from 4 to 10 bar, preferably from 5 to 9 bar and more preferably from 5 to 8 bar, and vaporized completely by introduction of heat. For example, about half the cold of expansion of the propene is produced by means of this step.

Accordingly, the present invention also provides a method of separating propylene oxide from a mixture (M) as described above, said method additionally comprising (viii) depressurizing a compressed propene stream into the at least one heat exchanger in (vii), vaporizing the propene stream in the at least one heat exchanger and preferably subsequently using the propene as reactant in a reaction comprising reacting propene with hydrogen peroxide in methanol as solvent and in the presence of a titanium zeolite fixed-bed catalyst.

The depressurization of the compressed stream in (vii) preferably takes place into a heat exchanger which can have essentially any configuration. Examples of configurations of the heat exchanger are shell-and-tube heat exchangers, coil heat exchangers or plate heat exchangers. For the purposes of the present invention, preference is given to using a heat exchanger which is configured as a shell-and-tube heat exchanger.

The bottoms stream obtained from (iii) can, according to a further embodiment of the method of the present invention, likewise be used for improving the energy integration of the method of the present invention even further.

For this purpose, the quantity of heat contained in the bottom stream obtained from (iii) is at least partly used for heating the mixture (M) before it is introduced into the extractive distillation column in (i). Particular preference is given to using a heat exchanger configured as a countercurrent heat exchanger (plate heat exchanger).

Accordingly, the present invention also provides a method of separating propylene oxide from a mixture (M) as described above wherein the energy stored in the bottom stream obtained from (iii) is at least partly used for heating or preheating the mixture (M) before said mixture is introduced into the extractive distillation column in (i).

The bottoms stream withdrawn from the extractive distillation column in (iii) may be used as such or after at least one work up step in at least one other process or may be recirculated in the method of the present invention. According to a preferred embodiment of the present invention, the bottoms stream is worked up in one, two or more steps to give a mixture comprising at least 97 percent by weight of methanol, not more than 2 percent by weight of water and not more than 50 ppm of acetaldehyde, based on the total weight of said mixture, and the methanol thus purified is recirculated in the method of the present invention, preferably as solvent for the epoxidation reaction the mixture (M) results from.

Depending on the polar solvent added in (ii) as extracting solvent, this solvent may be suitably separated from the bottoms stream and recirculated in the method of the present invention, preferably as polar solvent in (ii). A further advantage of the preferred method of the present invention according to which water is used as polar solvent, working up the bottoms stream obtained in (iii) so as to obtain the purified polar solvent to be recirculated in (ii) is not necessary since water is cheaply available, contrary to, e.g., propylene glycol described in U.S. Pat. No. 5,849,938 as preferred extracting solvent.

Moreover, the present invention also provides a method of preparing propylene oxide, said reaction comprising reacting propene with a hydroperoxide, preferably hydrogen peroxide in methanol as solvent and in the presence of a heterogeneous catalyst, preferably a zeolite catalyst, more preferably a titanium zeolite catalyst and especially preferably a titanium zeolite fixed-bed catalyst, said reaction resulting in a mixture (M) comprising 5 to 15 percent by weight propylene oxide, 50 to 85 percent by weight methanol, and 10 to 25 percent by weight water, or a mixture being worked up to give said mixture (M), said method further comprising (i) introducing said mixture (M) into an extractive distillation column;

(ii) additionally introducing water into said extractive distillation column in an amount of up to 2 percent by weight, preferably of 0.45 to 1 percent by weight of the mixture (M);

(iii) distilling propylene oxide overhead from said extractive distillation column as top stream at a pressure of from 300 to 750 mbar, preferably from 300 to 500 mbar and especially preferably from 450 to 500 mbar, and a bottoms temperature of from 40 to 70° C., preferably of from 40 to 60° C., and more preferably from 50 to 60° C., said top stream preferably comprising 100 ppm methanol or less;

(iv) optionally withdrawing a bottoms stream from said extractive distillation column and preferably using the energy stored in the bottom stream at least partly for heating the mixture (M) before said mixture is introduced into the extractive distillation column in (i);

(v) compressing the top stream obtained overhead in (iii) to a pressure of from more than 1.5 bar, preferably from more than 1.5 bar to 5 bar, more preferably from 2 to 4 bar and especially preferably from 2.5 to 3.5 bar by means of at least one compressor to give a compressed vapor, (vi) condensing the compressed vapor obtained in (v) and returning at least part of the heat of condensation to at least one vaporizer employed in the extractive distillation column used for distillation in (iii), (vii) cooling at least part of the condensate obtained in (vi) to a temperature in the range from preferably 10 to 30° C. in at least one heat exchanger and returning this part of the cooled condensate as reflux to the distillation column used in (iii) in an amount so that the mass ratio of reflux to distillate, obtained overhead in (iii), is 4 or less;

(viii) depressurizing a compressed propene stream into the at least one heat exchanger in (vii), vaporizing the propene stream in the at least one heat exchanger and subsequently using the propene as reactant in said epoxidation reaction comprising reacting propene with a hydroperoxide, preferably hydrogen peroxide in methanol as solvent and in the presence of a heterogeneous catalyst, preferably a zeolite catalyst, more preferably a titanium zeolite catalyst and especially preferably a titanium zeolite fixed-bed catalyst.

The following examples and figures are used to illustrate the present invention and are not meant to be limiting.

DETAILED DESCRIPTION OF THE FIGURES

FIG. 1 shows a preferred embodiment according to the invention. A mixture (M) and an extracting solvent (1) are introduced into an extractive distillation column (K100) (steps (i) and (ii)). Propylene oxide is distilled overhead from (K100) as top stream (step (iii)) which is compressed in the compressor (C100) (step (v)), and the compressed vapor stream is condensed in a heat exchanger (W100) where at least part of the heat of condensation is transferred to a reboiler employed in the extractive distillation column (K100) (step (vi)). The heat exchanger (W110) as shown in FIG. 1 is only used for starting the distillation process, i.e., during a preferred continuous distillation process according to the invention, heat exchanger (W110) is not used. The cooled and condensed stream leaving the heat exchanger (W100) is then divided, and a part of the stream is passed to a first heat exchanger (W130). The cooled stream leaving heat exchanger (W130) is then passed to a second heat exchanger (W140) where the stream is cooled further and ultimately recirculated as reflux on the top of the column (K100). Passing the stream through heat exchangers (W130) and (W140) represents step (vii) according to the invention where, as at least one heat exchanger, two heat exchangers are employed. According to a preferred embodiment of the invention, heat exchanger (W140) is used for depressurizing a compressed propene stream according to step (viii) of the present invention. If necessary and/or desired, part of the energy stored in the bottom stream obtained from (iii) may be used in a further heat exchanger (W120) where the mixture (M) is heated or preheated before it is introduced into column (K100) according to step (i).

Figure 2:
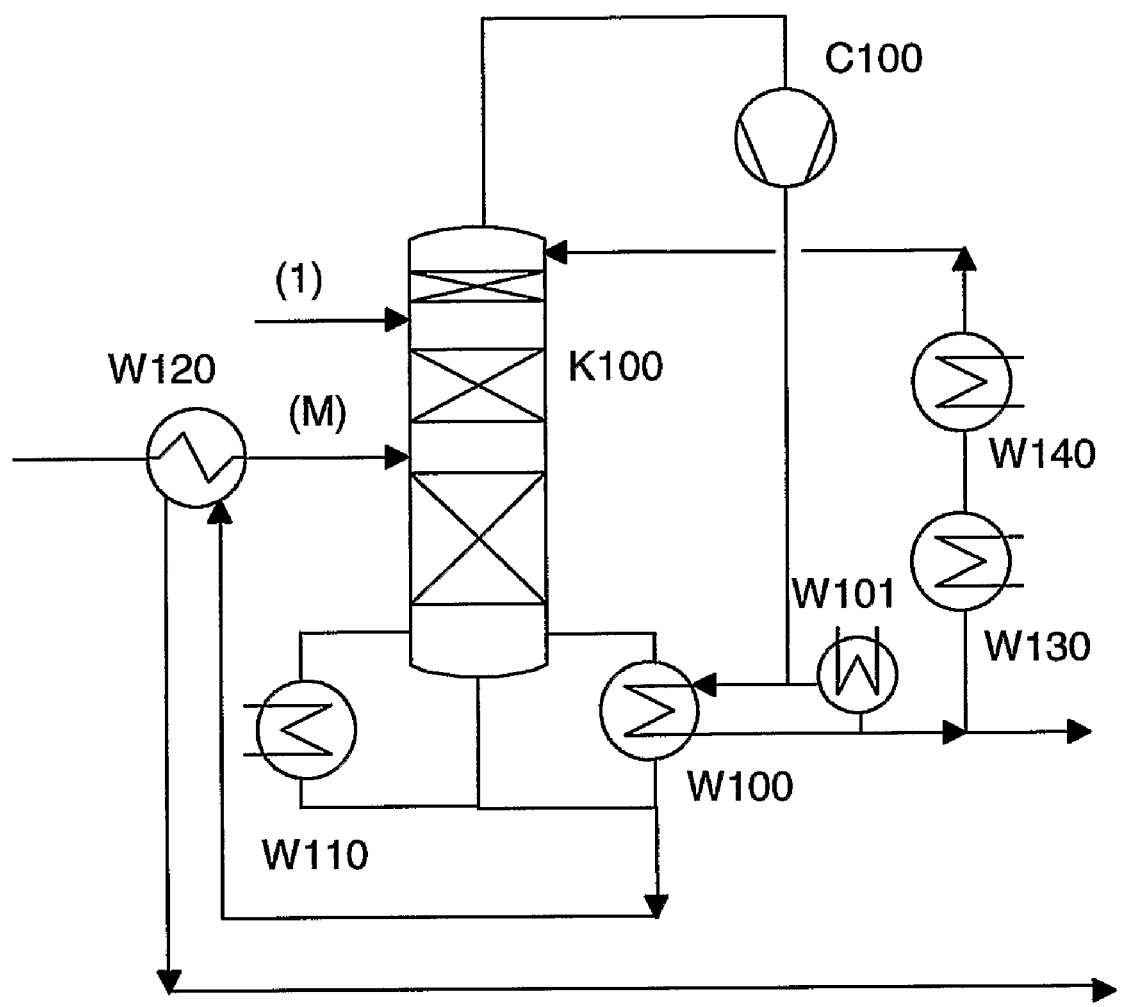

FIG. 2 shows another preferred embodiment of the present invention. In contrast to the process depicted in FIG. 1, the process according to FIG. 2 encompasses a further heat exchanger (W101). Depending on the amount of energy which shall be withdrawn from the compressed vapor stream and be transferred to a reboiler employed in the extractive distillation column (K100) (step (vi)), it might be necessary to divide the compressed vapor stream, and pass one part of the stream to heat exchanger (W100) and one part to heat exchanger (W101).

Figure 3:
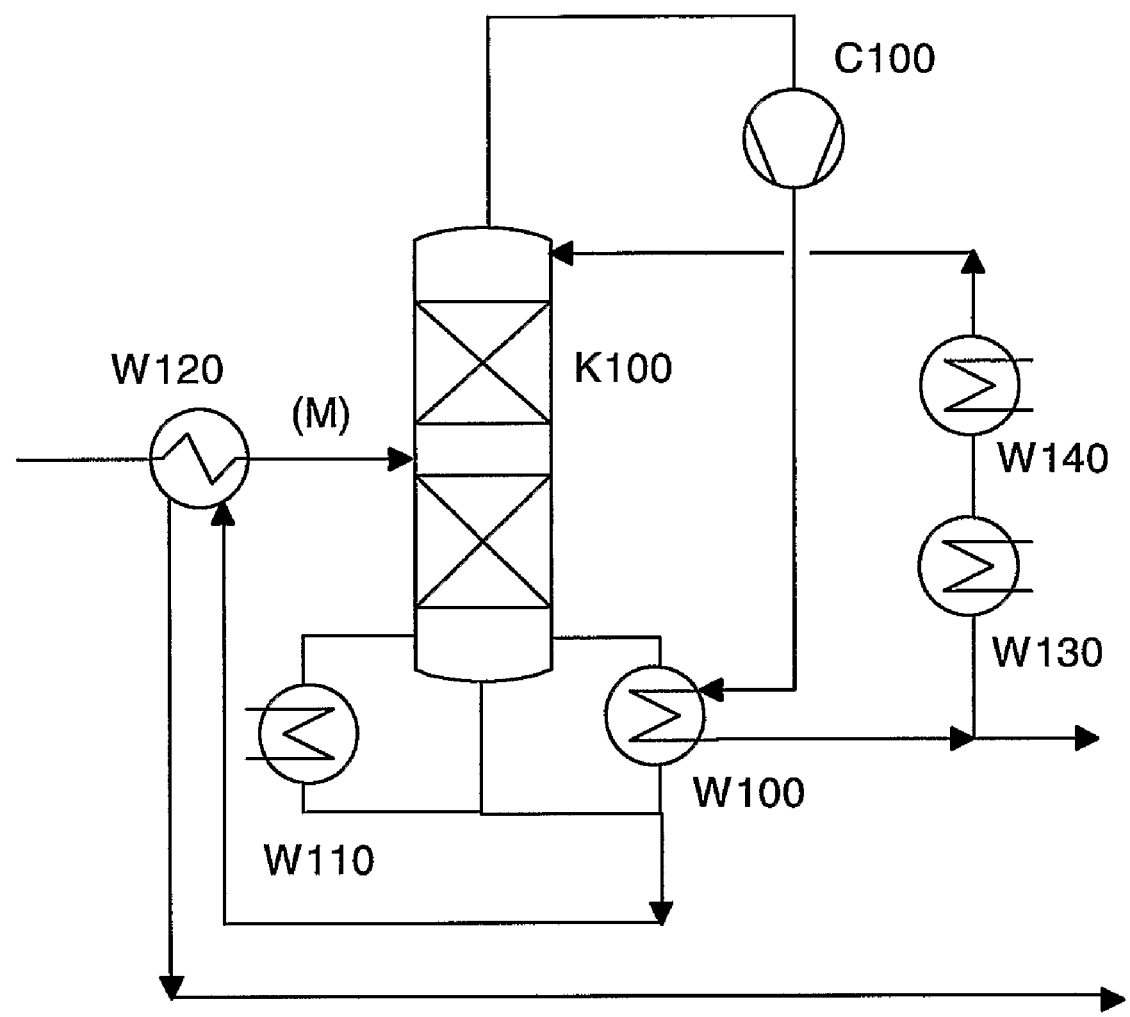

FIG. 3 corresponds to FIG. 1. However, no extracting solvent is used in the process as depicted in FIG. 3. Therefore, FIG. 3 represents a process according to the prior art.

Figure 4:
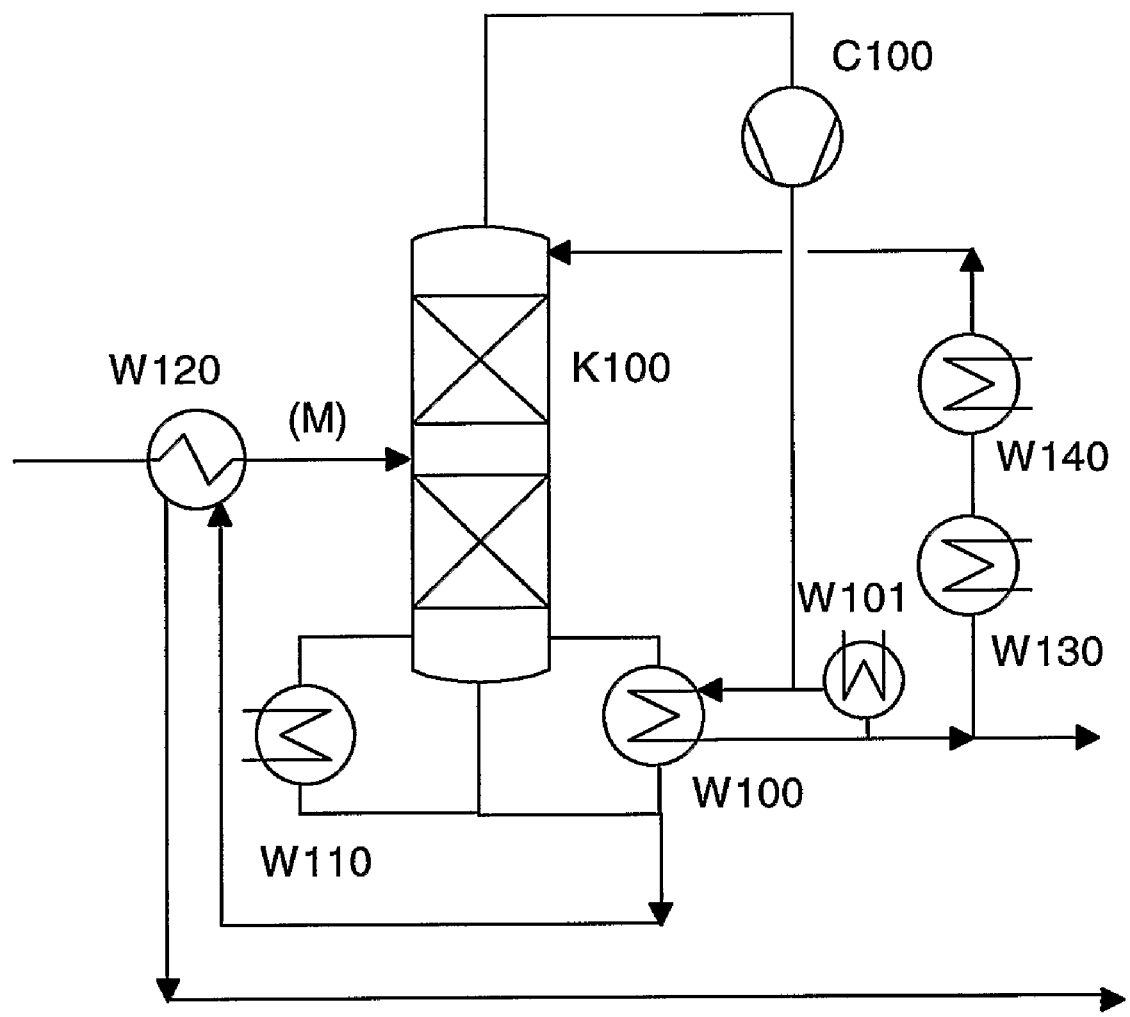

FIG. 4 corresponds to FIG. 2. However, no extracting solvent is used in the process as depicted in FIG. 4. Therefore, FIG. 4 represents a process according to the prior art.

Figure 5:
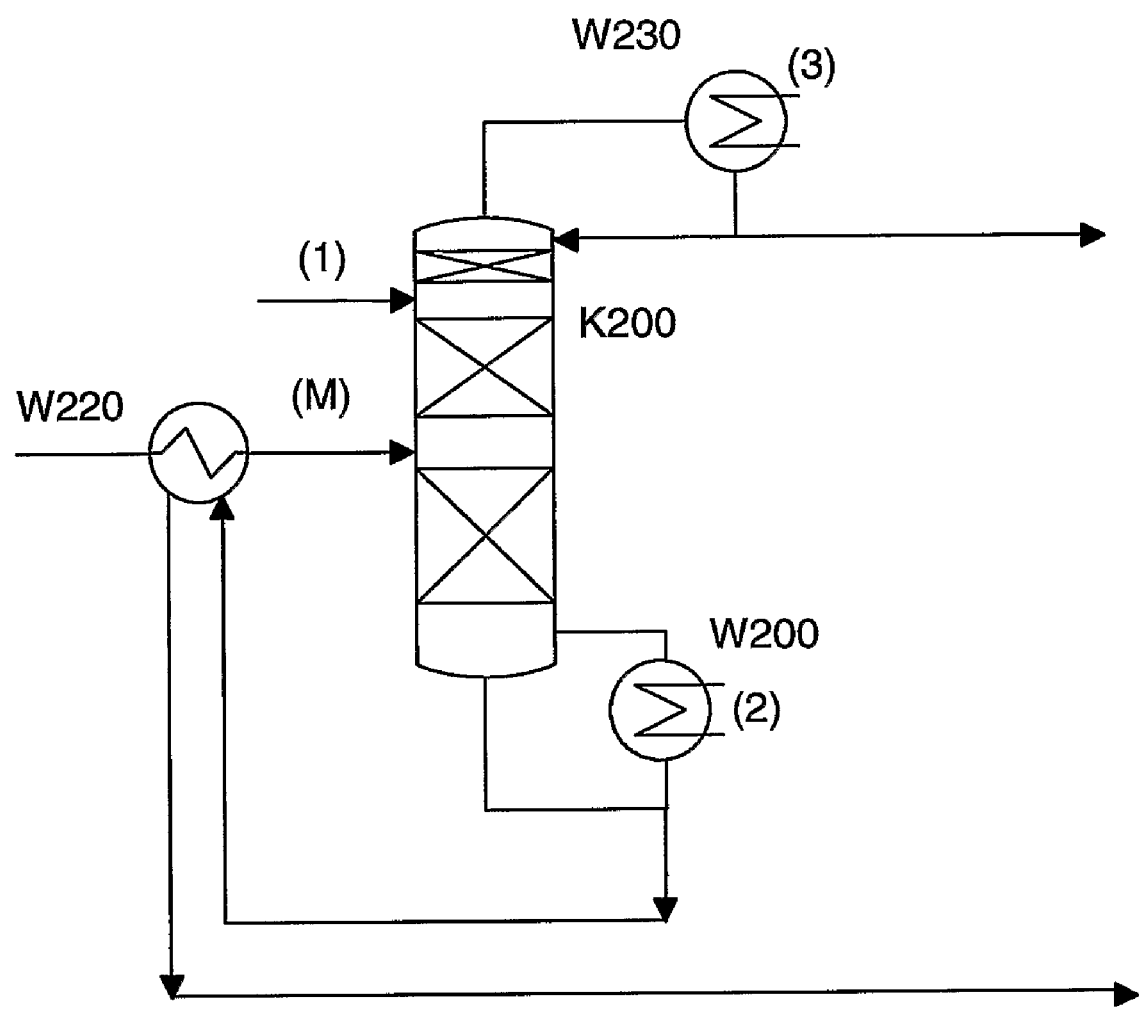

FIG. 5 shows a process where a heat exchanger (W230) is used to condense the top stream of an extractive distillation column (K200). As cooling agent (3) used in the heat exchanger (W230), chilled water and cooling water, respectively, are employed. To heat the reboiler of the column (K200), a heat exchanger (W200) is employed, and low pressure steam (2) is used as heating source. Heat exchanger (W220) is used to preheat mixture (M) before it is introduced into the column (K200).

EXAMPLES

A stream, the outlet of an epoxidation unit from which nearly all light boiling components were separated off, is subjected to different PO/MeOH separation units (examples 1 to 5). In all examples, this stream has the composition according to table 1:

TABLE 1 composition of stream

| stream | mass % |
|---|---|
| propylene | 0.013423 |
| formaldehyde | 0.011839 |
| acetaldehyde | 0.026834 |
| propylene oxide | 9.446765 |
| methanol | 71.97108 |
| water | 17.54493 |
| glycol ethers | 0.43074 |
| propylene glycol | 0.051477 |
| others (heavy boilers) | add to 100 |

Example 1

Extractive Distillation in Vacuo with Water and Compressing Top Stream

The process of example 1 is carried out in a unit of apparatuses as shown in FIG. 1, resp. FIG. 2.

The above described stream (table 1) is fed to an extractive distillation tower (K100) containing 80 theoretical stages, equipped with an electric compressor (C100) to compress the top vapour outlet stream of the top of the column. The compressed stream is used as heating source for a reboiler of the distillation column. For this, a heat exchanger (W100) is employed. The column (K100) is operated in vacuo at a pressure of 500 mbar. Water is used as extracting solvent (1).

The feeding points are as follows: the feed stream of the column is fed on stage 45 stage from the top of the column, water is fed on stage 12 from the top of the column. The flow rate of the extracting agent water is 5.2% with respect to the propylene oxide contained in the feed stream.

Purified propylene oxide is obtained at the top of the tower. The tower is operated at a mass reflux ratio (reflux:distillate) of 3.9. The reboiler duty is 22 MW.

The top propylene oxide stream contains, beside the light boiler contaminations, 10 ppm of MeOH and 55 ppm of water. The bottom stream contains only 50 ppm of propylene oxide, MeOH, water and all other heavy boilers.

Due to the use of the compressed top vapour stream as a heating source for the reboiler, the column can be operated without any external heating stream.

In the present case, water is used as extracting solvent. Thus, no water recycle loop is necessary since water leaves the plant (together with the water obtained as by-product of the epoxidation reaction and, if an aqueous hydrogen peroxide was used for the initial epoxidation process, the water comprised in this aqueous solution) and can be treated without any additional costs in a waste water treatment plant.

This configuration is a very effective and economic way to separate propylene oxide and MeOH.

Example 2

Extractive Distillation in Vacuo with Propylene Glycol and Compressing Top Stream The process of example 2 is carried out in a unit of apparatuses as shown in FIG. 1 resp. FIG. 2.

The above described stream (table 1) is fed to an extractive distillation tower (K100) containing 80 theoretical stages, equipped with an electric compressor (C100) to compress the top vapour outlet stream of the top of the column. The compressed stream is used as heating source for a reboiler of the distillation column. For this, a heat exchanger (W100) is employed. The column (K100) is operated in vacuo at a pressure of 500 mbar. Propylene glycol is used as extracting solvent (1).

The feeding points are as follows: the feed stream of the column is fed on stage 60 stage from the top of the column, propylene glycol is fed on stage 2 from the top of the column. The flow rate of the extracting agent propylene glycol is 15.4% with respect to the propylene oxide contained in the feed stream.

Purified propylene oxide is obtained at the top of the tower. The tower is operated at a mass reflux ratio (reflux:distillate) of 4.7. The reboiler duty is 25.5 MW.

The top propylene oxide stream contains, beside the light boiler contaminations, 10 ppm of MeOH and not more than 1 ppm of water. The bottom stream contains 50 ppm of propylene oxide, MeOH, water, the added propylene glycol and all other heavy boilers.

Due to the use of the compressed top vapour stream as a heating source for the reboiler, the column can be operated without any external heating stream.

To obtain an additional economical benefit from the use of propylene glycol as extracting solvent, propylene glycol must be recycled. This inevitably causes additional costs, compared to the use of water as extracting solvent.

The comparison of this two examples shows that water is a more effective extracting solvent than propylene glycol.

Example 3

Extractive Distillation with (A) Water and (B) Propylene Glycol at 2 Bar without Compressing Top Stream Comparative Examples The processes of example 3 are carried out in a unit of apparatuses as shown in FIG. 5. In FIG. 5, a heat exchanger (W230) is shown in which the top stream of an extractive distillation column (K200) is cooled using chilled water and cooling water, respectively. To heat the reboiler of the column, a heat exchanger (W200) is employed, and low pressure steam is used as heating source. Heat exchanger (W220) is used to preheat mixture (M), i.e. the feed according to table 1, before it is introduced into the column (K200).

(a) The above described stream (table 1) is fed to an extractive distillation tower (K200) containing 80 theoretical stages. The column (K200) is operated at a pressure of 2 bar. Water is used as extracting solvent (1). Due to the fact that no compression of the top stream is carried out, low pressure steam must be used as an external heating source to heat the reboiler of the column. The condenser (W230) is operated with cooling tower water. The reboiler duty is 31.5 MW, the condenser duty 30.2 MW. The feeding points are as follows: the feed stream of the column is fed on stage 50 from the top of the column, water as extracting agent is fed on stage 12 from the top of the column, at a flow rate of 10.4% with respect to the propylene oxide contained in the feed stream. The tower is operated at a mass reflux ratio (reflux:distillate) of 6.1. Purified propylene oxide is taken at the top of the tower. The top propylene oxide stream contains, beside the light boilers, 10 ppm of MeOH and 1,500 ppm of water. The bottom stream contains 50 ppm of propylene oxide, MeOH, water and all other heavy boilers.

b) The above described stream (table 1) is fed to an extractive distillation tower (K200) containing 80 theoretical stages. The column (K200) is operated at a pressure 2 bar. Propylene glycol is used as extracting solvent (1). Due to the fact that no compression of the top stream is carried out, low pressure steam must be used as an external heating source to heat the reboiler of the column. The condenser (W230) is operated with cooling tower water. The reboiler duty is 36.5 MW, the condenser duty 34.5 MW. The feedings point are as follows: the feed stream of the column is fed on stage 60 from the top of the column, propylene glycol as extracting agent is fed on stage 2 from the top of the column, at a flow rate of 30% with respect to the propylene oxide contained in the feed stream. The tower is operated at a mass reflux ration (reflux:distillate) of 7.3. Purified propylene oxide is taken at the top of the tower. The top propylene oxide stream contains, beside the light boilers, 10 ppm of MeOH. The bottom stream contains 50 ppm of propylene oxide, MeOH, water, the added propylene glycol and all other heavy boilers.

Example 4

Fractional Distillation without Polar Solvent Including Compressing Top Stream

Comparative Example

The process of example 4 is carried out in a unit of apparatuses as shown in FIG. 3 resp. FIG. 4.

The above described stream (table 1) is fed to a distillation tower (K100) containing 80 theoretical stages, equipped with a compressor (C100) to compress the top vapour outlet stream of the top of column. This stream is used as a heating source for the reboiler of the distillation column. The column is operated in vacuo at 500 mbar. No extracting solvent is used. The feeding point of the feed stream is on stage 68 from the top of the column. Purified propylene oxide is taken at the top of the tower. The tower is operated at a mass reflux ratio (reflux:distillate) of 9.4. The reboiler duty is 49.5 MW. The top propylene oxide stream contains beside the lights 10 ppm of MeOH. The bottom stream contains 50 ppm of propylene oxide, MeOH, water and all the other heavies.

The comparison of examples 1 and 4 shows the effect of water as extracting solvent. Using water as extracting solvent, the reboiler duty and consequently the size of the compressor can be reduced by about 50%.

Example 5

Extractive Distillation with Water In Vacuo but without Compression of Top Stream Comparative Example The process of example 5 is carried out in a unit of apparatuses as shown in FIG. 5.

The above described stream (table 1) is fed to an extractive distillation tower (K200) containing 80 theoretical stages. Low pressure steam is used to heat the reboiler of the column via heat exchanger (W200). The condenser (W230) is operated with chilled water, which has to be prepared in a chilled water unit (not shown). The column (K200) is operated in vacuo at 500 mbar. Water is used as extracting solvent (1). The feeding point are as follows: feed stream of the column is fed on stage 45 from the top of the column, water as extracting solvent is fed on stage 12 from the top of the column, at a flow rate of 5.2% with respect to the propylene oxide contained in the feed stream. Purified propylene oxide is taken at the top of the tower. The tower is operated at a mass reflux ratio (reflux:distillate) of 3.9. The top propylene oxide stream contains, beside the light boilers, 10 ppm of MeOH and 55 ppm of water. The bottom stream contains 50 ppm of propylene oxide, MeOH, water and all other heavy boilers.

The following table 2 gives an overview of the described examples:

TABLE 2 overview of the described examples.

|  | example | | | | | |
| --- | --- | --- | --- | --- | --- | --- |
|  | 1 | 2 | 3a | 3b | 4 | 5 |
| extracting solvent | water | propylene glycol | water | propylene glycol | — | water |
| top pressure [bar] | 0.5 | 0.5 | 2 | 2 | 0.5 | 0.5 |
| top temperature [° C.] | 16.1 | 16.1 | 54.8 | 54.8 | 16.1 | 16.1 |
| compression of top vapor stream | yes | yes | no | no | yes | no |
| theoretical stages | 80 | 80 | 80 | 80 | 80 | 80 |

TABLE 2-continued overview of the described examples.

| | example | | | | | |
|---|---|---|---|---|---|---|
| | 1 | 2 | 3a | 3b | 4 | 5 |
| feeding point (from top) | 45 | 60 | 50 | 62 | 68 | 45 |
| feeding point extracting solvent (from top) | 12 | 2 | 12 | 2 | — | 12 |
| mass ratio extr. solvent/propylene oxide [%] | 5.2 | 15.4 | 10.4 | 30 | — | 5.2 |
| mass reflux ratio | 3.9 | 4.7 | 6.1 | 7.3 | 9.4 | 3.9 |
| bottom temperature of (K100/200) [° C.] | 55.9 | 55.9 | 89.5 | 91.5 | 55.8 | 55.9 |
| propylene oxide traces in bottom stream [ppm] | 50 | 50 | 50 | 50 | 50 | 50 |
| MeOH traces in distillate stream [ppm] | 10 | 10 | 10 | 10 | 10 | 10 |
| reboiler duty [MW] of (K100) or (K200) | 22 | 25.5 | 31.5 | 36.5 | 49.5 | 22 |
| electr. condenser energy consumption [MW] (C100) | 6 | 7.3 | — | — | 14.5 | — |
| condenser capacity cooling tower water [MW] (W230) | — | — | 30.2 | 34.5 | — | — |
| condenser capacity chilled water [MW] (W230) | — | — | — | — | — | 21.1 |
| cooling tower water [MW] (W130) | 2.5 | 3.0 | — | — | 6.0 | — |
| chilled water [MW] (W140) | 1.5 | 1.8 | — | — | 3.6 | — |
| heating source of reboiler of column (K100) or (K200) | compressed top stream vapor | compressed top stream vapor | low pressure steam | low pressure steam | compressed top stream vapour | low pressure steam |

We claim:

1. A method of separating propylene oxide from a mixture (M) comprising propylene oxide and methanol, said method comprising
    (i) introducing said mixture (M) into an extractive distillation column;
    (ii) additionally introducing an extracting solvent into said extractive distillation column;
    (iii) distilling propylene oxide overhead from said extractive distillation column as top stream;
    (iv) withdrawing a bottoms stream from said extractive distillation column;
    (v) compressing the top stream obtained overhead in (iii) by means of at least one compressor to give a compressed vapor.

2. The method as claimed in claim 1, wherein, in (iii), the distillation is carried out at a pressure of 1.5 bar or less, and, in (v), the top stream is compressed to a pressure of more than 1.5 bar.

3. The method as claimed in claim 2, wherein, in (iii), the distillation is carried out at a pressure of from 300 to 750 mbar and a bottoms temperature of from 40 to 70° C., and, in (v), the top stream is compressed to a pressure of from 2 to 4 bar.

4. The method as claimed in claim 1, additionally comprising
    (vi) condensing the compressed vapor obtained in (v) and returning at least part of the heat of condensation to at least one reboiler employed in the extractive distillation column.

5. The method as claimed in claim 4, additionally comprising
    (vii) cooling at least part of the condensate obtained in (vi) to a temperature in the range from 10 to 30° C. in at least one heat exchanger and returning this part of the cooled condensate as ref lux to the extractive distillation column used in (iii).

6. The method as claimed in claim 5, additionally comprising
    (viii) depressurizing a compressed propene stream into the at least one heat exchanger in (vii), vaporizing the propene stream in the at least one heat exchanger and subsequently using the propene as reactant in a reaction comprising reacting propene with hydrogen peroxide in methanol as solvent and in the presence of a titanium zeolite fixed-bed catalyst.

7. The method as claimed in claim 1, wherein the energy stored in the bottom stream obtained in (iv) is at least partly used for heating or preheating the mixture (M) before said mixture is introduced into the extractive distillation column in (i).

8. The method as claimed in claim 1, wherein the mixture (M) is formed in a reaction comprising reacting propene with hydrogen peroxide in methanol as solvent and in the presence of a titanium zeolite fixed-bed catalyst.

9. The method as claimed in claim 1, wherein water is used as extracting solvent.

10. The method as claimed in claim 9, wherein the water is introduced as vapor at a pressure of not more than 2 bar.

11. The method as claimed in claim 1, wherein said mixture (M) comprises 5 to 50 percent by weight propylene oxide and 50 to 85 percent by weight methanol.

12. The method as claimed in claim 11, said mixture (M) comprising 5 to 15 percent by weight propylene oxide and additionally comprising 10 to 25 percent by weight water.

13. The method as claimed in claim 1, wherein the extracting solvent is introduced in an amount of 2 percent by weight, based on the total weight of the mixture (M), or less.

14. The method as claimed in claim 1, wherein the extractive distillation column has up to 80 theoretical plates.

15. The method as claimed in claim 5, wherein the mass ratio of reflux to distillate, obtained as top stream in (iii), is 4.9 or less.

16. The method as claimed in claim 1, wherein the top stream distilled overhead comprises 100 ppm methanol or less and the bottoms stream withdrawn from the extractive distillation column has a propylene oxide content of 100 ppm or less.

17. A method of separating propylene oxide from a mixture (M) comprising 5 to 15 percent by weight propylene oxide, 50 to 85 percent by weight methanol, and 10 to 25 percent by weight water, said method comprising
  (i) introducing said mixture (M) into an extractive distillation column having up to 80 theoretical plates;
  (ii) additionally introducing water as an extracting solvent into said extractive distillation column;
  (iii) distilling propylene oxide overhead from said extractive distillation column as top stream, the distillation being carried out at a pressure of from 300 to 750 mbar and a bottoms temperature of from 40 to 70° C., wherein the mass ratio of reflux to distillate, obtained as top stream in (iii), is 4.9 or less;
  (iv) withdrawing a bottoms stream from said extractive distillation column, the bottoms stream having a propylene oxide content of 100 ppm or less;
  (v) compressing the top stream obtained overhead in (iii) which comprises 100 ppm methanol or less, by means of at least one compressor to give a compressed vapor, the top stream being compressed to a pressure of from 2 to 4 bar;
  (vi) condensing the compressed vapor obtained in (v) and returning at least part of the heat of condensation to at least one reboiler employed in the extractive distillation column;
  (vii) cooling at least part of the condensate obtained in (vi) to a temperature in the range from 10 to 30° C. in at least one heat exchanger and returning this part of the cooled condensate as reflux to the extractive distillation column used in (iii),
  wherein the energy stored in the bottom stream obtained in (iv) is at least partly used for heating or preheating the mixture (M) before said mixture is introduced into the extractive distillation column in (i).

18. The method as claimed in claim 17, additionally comprising
  (viii) depressurizing a compressed propene stream into the at least one heat exchanger in (vii), vaporizing the propene stream in the at least one heat exchanger and subsequently using the propene as reactant in a reaction comprising reacting propene with hydrogen peroxide in methanol as solvent and in the presence of a titanium zeolite fixed-bed catalyst.

19. The method as claimed in claim 17, wherein the mixture (M) is formed in a reaction comprising reacting propene with hydrogen peroxide in methanol as solvent and in the presence of a titanium zeolite fixed-bed catalyst.

* * * * *